(12) United States Patent
Kehler et al.

(10) Patent No.: US 9,216,986 B1
(45) Date of Patent: Dec. 22, 2015

(54) QUINOLINE DERIVATIVES AS PDE10A ENZYME INHIBITORS

(71) Applicant: H. Lundbeck A/S, Valby (DK)

(72) Inventors: Jan Kehler, Lyngby (DK); Jacob Nielsen, København V. (DK); Ask Püschl, Frederiksberg C. (DK); John Paul Kilburn, Haslev (DK); Morten Langgård, Glostrup (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/305,736

(22) PCT Filed: Dec. 21, 2012

(86) PCT No.: PCT/EP2012/076590
§ 371 (c)(1),
(2) Date: Jul. 17, 2014

(87) PCT Pub. No.: WO2013/092974
PCT Pub. Date: Jun. 27, 2013

Related U.S. Application Data

(60) Provisional application No. 61/578,320, filed on Dec. 21, 2011.

(30) Foreign Application Priority Data

Dec. 21, 2011 (DK) .................... PA 2011 00990

(51) Int. Cl.
*C07D 487/04* (2006.01)
*C07D 471/04* (2006.01)

(52) U.S. Cl.
CPC ............ *C07D 487/04* (2013.01); *C07D 471/04* (2013.01)

(58) Field of Classification Search
None
See application file for complete search history.

(56) References Cited

FOREIGN PATENT DOCUMENTS

WO   2011/150156 A2   12/2011

OTHER PUBLICATIONS

Campbell et al., WO2011/150156 (CAS Abstract).*
International Search Report and Written Opinion issued Feb. 19, 2013 in International Application No. PCT/ER2012/076590 filed Dec. 21, 2012.

* cited by examiner

*Primary Examiner* — Timothy R Rozof
(74) *Attorney, Agent, or Firm* — Mary Catherine Di Nunzio

(57) ABSTRACT

The present invention provides quinoline derivatives of formula I that are PDE10A enzyme inhibitors, and as such are useful to treat neurodegenerative and psychiatric disorders. Especially, the invention provides compounds that are highly selective for PDE10 over other PDE subtypes. The present invention also provides pharmaceutical compositions comprising compounds of the invention and methods of treating disorders using the compounds of the invention.

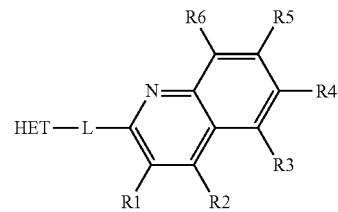

10 Claims, No Drawings

QUINOLINE DERIVATIVES AS PDE10A ENZYME INHIBITORS

CROSS-REFERENCE TO RELATED APPLICATIONS

The present application is a U.S. national stage application of PCT International Application No. PCT/EP12/076590 filed, Dec. 21, 2012, which claims priority of U.S. Provisional Application No. 61/578,320, filed Dec. 21, 2011 and Danish Application No. PA201100990 filed, Dec. 21, 2011.

FIELD OF THE INVENTION

The present invention provides quinoline derivatives that are PDE10A enzyme inhibitors, and as such are useful to treat neurodegenerative and psychiatric disorders. Especially, the invention provides compounds that are highly selective for PDE10 over other PDE subtypes. The present invention also provides pharmaceutical compositions comprising compounds of the invention and methods of treating disorders using the compounds of the invention.

BACKGROUND OF THE INVENTION

The cyclic nucleotides cyclic-adenosine monophosphate (cAMP) and cyclic-guanosine monophosphate (cGMP) function as intracellular second messengers regulating a vast array of processes in neurons. Intracellular cAMP and cGMP are generated by adenyl and guanyl cyclases, and are degraded by cyclic nucleotide phosphodiesterases (PDEs) via hydrolysis of the cyclic nucleotides into their respective nucleotide monophosphates.

Phosphodieasterase 10A (PDE10A) is a dual-specificity phosphodiesterase that can convert both cAMP to AMP and cGMP to GMP (Soderling, S. et al. *Proc. Natl. Acad. Sci.* 1999, 96, 7071-7076). PDE10A is primarily expressed in the neurons in the striatum, n. accumbens and in the olfactory tubercle (Kotera, J. et al. *Biochem. Biophys. Res. Comm.* 1999, 261, 551-557 and Seeger, T. F. et al. *Brain Research,* 2003, 985, 113-126).

Studies indicate that within the brain, PDE10 expression is expressed at high levels by the medium spiny neurons (MSN) of the caudate nucleus, the accumbens nucleus and the corresponding neurons of the olfactory tubercle. MSN express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway.

Dopamine $D_2$ receptor antagonism is well established in the treatment of schizophrenia. Since the 1950's, dopamine $D_2$ receptor antagonism has been the mainstay in psychosis treatment and all effective antipsychotic drugs antagonise $D_2$ receptors. The effects of $D_2$ are likely to be mediated primarily through neurons in the striatum, nucleus accumbens and olfactory tubercle, since these areas receive the densest dopaminergic projections and have the strongest expression of $D_2$ receptors (Konradi, C. and Heckers, S. *Society of Biological Psychiatry,* 2001, 50, 729-742).

Because PDE10A, in this context, has the desired expression profile with high and relatively specific expression in neurons in striatum, nucleus accumbens and olfactory tubercle, PDE10A inhibition is likely to have effects similar to $D_2$ receptor antagonism and therefore have antipsychotic effects.

While PDE10A inhibition is expected to mimic $D_2$ receptor antagonism in part, it might be expected to have a different profile. The D2 receptor has signaling components besides cAMP (Neve, K. A. et al. *Journal of Receptors and Signal Transduction* 2004, 24, 165-205), wherefore interference with cAMP through PDE10A inhibition may reduce the risk of the extrapyramidal side effects that are seen with strong $D_2$ antagonism. Conversely, PDE10A inhibition may have some effects not seen with $D_2$ receptor antagonism. PDE10A is also expressed in $D_1$ receptors expressing striatal neurons (Seeger, T. F. et al. *Brain Research,* 2003, 985, 113-126).

Further, since $D_1$ receptor agonism leads to stimulation of adenylate cyclase and resulting increase in cAMP levels, PDE10A inhibition is likely to also have effects that mimic $D_1$ receptor agonism.

Finally, PDE10A inhibition will not only increase cAMP in cells, but might also be expected to increase cGMP levels, since PDE10A is a dual specificity phosphodiesterase. cGMP activates a number of target protein in cells like cAMP and also interacts with the cAMP signaling pathways.

In conclusion, PDE10A inhibition is likely to mimic $D_2$ receptor antagonism in part and therefore has antipsychotic effect, but the profile might differ from that observed with classical $D_2$ receptor antagonists.

The PDE10A inhibitor papaverine is shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine induced hyperactivity was insignificant (WO 03/093499). These models suggest that PDE10A inhibition has the classic antipsychotic potential that would be expected from the theoretical considerations outlined above. WO 03/093499 further discloses the use of selective PDE10 inhibitors for the treatment of associated neurologic and psychiatric disorders. Furthermore, PDE10A inhibition reverses subchronic PCP-induced deficits in attentional set-shifting in rats (Rodefer et al. *Eur. J. Neurosci.* 2005, 4, 1070-1076). This model suggests that PDE10A inhibition might alleviate cognitive deficits associated with schizophrenia.

The tissue distribution of PDE10A indicates that PDE10A inhibitors can be used to raise levels of cAMP and/or cGMP within cells that express the PDE10A enzyme, especially neurons that comprise the basal ganglia, and the PDE10A inhibitors of the present invention would therefore be useful in treating a variety of associated neuropsychiatric conditions involving the basal ganglia such as neurological and psychiatric disorders, schizophrenia, bipolar disorder, psychosis, obsessive compulsive disorder and addiction, and may have the benefit of not possessing unwanted side effects, which are associated with the current therapies on the market.

Furthermore, recent publications (WO 2005/120514, WO 2005012485, Cantin et al, Bioorganic & Medicinal Chemistry Letters 17 (2007) 2869-2873) suggest that PDE10A inhibitors may be useful for treatment of obesity and non-insulin dependent diabetes.

Furthermore, recent publications suggest that PDE10A inhibitors may be useful for the treatment of Huntingtons Disease (Giampa et al. PLoS One 2010, 5(10), Giampa et al. Neurobiology of Disease (2009), 34(3), 450-456, Hebb et al. Current Opinion in Pharmacology 2007, 7(1), 86-92.)

Pyrrolodihydroisoquinolines and variants thereof are disclosed as inhibitors of PDE10 in WO 05/03129 and WO 05/02579. Piperidinyl-substituted quinazolines and isoquinolines that serve as PDE10 inhibitors are disclosed in WO 05/82883. WO 06/11040 discloses substituted quinazoline and isoquinoline compounds that serve as inhibitors of PDE10. US 20050182079 discloses substituted tetrahydroisoquinolinyl derivatives of quinazoline and isoquinoline that serve as effective phosphodiesterase (PDE) inhibitors. In particular, US 20050182079 relates to said compounds, which are selective inhibitors of PDE10. Analogously, US 20060019975 discloses piperidine derivatives of quinazoline and isoquinoline that serve as effective phosphodiesterase (PDE) inhibitors. US 20060019975 also relates to compounds that are selective inhibitors of PDE10. WO 06/028957 discloses cinnoline derivatives as inhibitors of PDE10 for the treatment of psychiatric and neurological syndromes. WO09/152825 discloses phenylimidazole derivatives as compounds that serve as inhibitors of PDE10.

However, these disclosures do not pertain to the compounds of the invention, which are structurally unrelated to any of the known PDE10 inhibitors (Kehler, J. et al. *Expert Opin. Ther. Patents* 2007, 17, 147-158), and which have now been found by the inventors to be highly active and selective PDE10A enzyme inhibitors.

The present invention provides compounds that are PDE10A enzyme inhibitors and thus useful for treatment for neurodegenerative and/or psychiatric disorders, which are not efficacious in all patients. Hence, there remains a need for alternative methods of treatment.

SUMMARY OF THE INVENTION

The objective of the present invention is to provide compounds that are selective PDE10A enzyme inhibitors.

A further objective of the present invention is to provide compounds which have such activity, and which have improved solubility, metabolic stability and/or bioavailability compared to prior art compounds.

Another objective of the invention is to provide an effective treatment, in particular long-term treatment, of a human patient, without causing the side effects typically associated with current therapies for neurological and psychiatric disorders.

Further objectives of the invention will become apparent upon reading the present specification.

DETAILED DESCRIPTION OF THE INVENTION

Embodiments of the Invention

In a first embodiment (E1) the present invention relates to compounds of formula I:

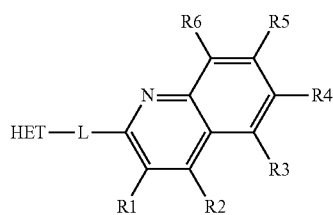

I wherein $R_1$, $R_2$, $R_3$, $R_4$, $R_5$ and $R_6$ are individually selected from the group consisting of hydrogen, hydroxyl, cyano, $C_1$-$C_6$ alkyl; $C_1$-$C_6$ alkoxy, halogen, methylenedioxy, diflouromethylenedioxy and ethylenedioxy wherein -L- is a linker selected from —$CH_2$—$CH_2$— and —CH=CH— wherein HET is selected from the group consisting of

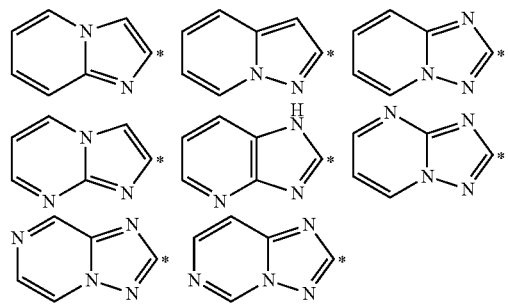

wherein one or more of the carbon-bound hydrogen in the HET optionally may be substituted with up to three substituents $R_7$, $R_8$ and $R_9$ individually selected from $C_1$-$C_6$ alkyl; halogen; cyano, halo($C_1$-$C_6$)alkyl; aryl, alkoxy and $C_1$-$C_6$ hydroxyalkyl and wherein * denotes the attachment point, and tautomers and pharmaceutically acceptable salts thereof, and polymorphic forms thereof.

In an embodiment (E2) of embodiment (E1) one or more of $R_1$-$R_6$ is selected from the group consisting of $C_1$-$C_3$ alkyl substituted with one or more F and unsubstituted $C_1$-$C_3$ alkyl.

In an embodiment (E3) of embodiment (E1) or (E2) one or more of $R_1$-$R_6$ is selected from the group consisting of methyl, ethyl, propyl, isopropyl, monoflouromethyl, diflouromethyl and triflouromethyl.

In an embodiment (E4) of embodiment (E1) one or more of $R_1$-$R_6$ is selected from the group consisting of methoxy, diflouromethoxy and triflouromethoxy.

In an embodiment (E5) of embodiment (E1) one or more of $R_1$-$R_6$ is selected from the group consisting of fluorine and chlorine.

In an embodiment (E6) of any of embodiments (E1) to (E5) -L- is —$CH_2$—$CH_2$—

In an embodiment (E7) of any of embodiments (E1) to (E5) -L- is —CH=CH—

In an embodiment (E8) of any of embodiments (E1) to (E7) HET is selected from the group consisting of

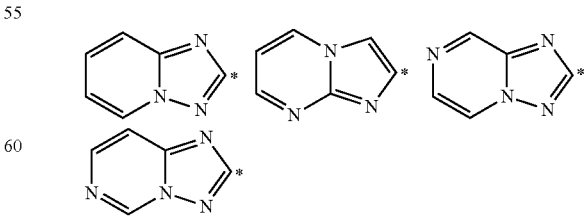

wherein HET optionally is substituted with one or more of R7-R9, and
wherein * denotes the attachment point.

In an embodiment (E9) of any of embodiments (E1) to (E8) HET is substituted with one substituent R7 selected from the group consisting of $C_1$-$C_6$ alkyl, such as methyl; halogen, such as chlorine or bromine; cyano; halo($C_1$-$C_6$)alkyl, such as trifluoromethyl; aryl such as phenyl; and $C_1$-$C_6$ hydroxyalkyl such as $CH_2CH_2OH$.

In an embodiment (E10) of any of embodiments (E1) to (E8), HET is substituted with two substituents R7 and R8 individually selected from $C_1$-$C_6$ alkyl, such as methyl; halogen, such as chlorine or bromine; cyano; halo($C_1$-$C_6$)alkyl, such as trifluoromethyl; aryl, such as phenyl; and $C_1$-$C_6$ hydroxyalkyl, such as $CH_2CH_2OH$.

In an embodiment (E11) of any of embodiment (E1) to (E8), HET is substituted with three substituents R7, R8 and R9 individually selected from $C_1$-$C_6$ alkyl, such as methyl; halogen, such as chlorine or bromine; cyano; halo($C_1$-$C_6$) alkyl, such as trifluoromethyl; aryl, such as phenyl; and $C_1$-$C_6$ hydroxyalkyl, such as $CH_2CH_2OH$.

In an embodiment (E12) of any of embodiments (E1) to (E8) HET is unsubstituted.

In an embodiment (E13) of any of embodiments (E1), (E9), (E10) and (E11) HET is substituted with at least one $C_1$-$C_6$ alkyl, such as methyl In an embodiment (E14) of any of embodiments (E1) to (E11) HET is selected from the group consisting of (5,7-Dimethyl-imidazo[1,2-a]pyrimidin-2-yl), 5,7-Dimethyl-[1,2,4]triazolo[1,5-a]pyrimidin-2-yl), (5,8-Dimethyl-[1,2,4]triazolo[1,5-a]pyrazin-2-yl), (8-Methoxy-5-methyl-[1,2,4]triazolo[1,5-a]pyridin-2-yl) and 5,8-Dimethyl-[1,2,4]triazolo[1,5-a]pyridin-2-yl).

In a specific embodiment (E15) of embodiment (E1) the compound is selected from the group of compounds listed in Table 1.

In an embodiment (E16) of any of the embodiments (E1) to (E15) the invention provides a compound of formula I, or a pharmaceutically acceptable salt thereof, for use as a medicament.

In an embodiment (E17) of any of the embodiments (E1) to (E15) the invention provides a pharmaceutical composition comprising a therapeutically effective amount of a compound of formula I and a pharmaceutically acceptable carrier, diluent or excipient.

In an embodiment (E18) of any of the embodiments (E1) to (E15) the present invention provides the use of a compound of formula I, or a pharmaceutically acceptable salt thereof, for the preparation of a medicament for the treatment of a neurodegenerative or psychiatric disorder.

Furthermore, in an embodiment (E19) of any of the embodiments (E1) to (E15) the present invention provides a method of treating a subject suffering from a neurodegenerative disorder, comprising administering to the subject a therapeutically effective amount of a compound of formula I.

In an embodiment (E20) of any of the embodiments (E1) to (E15) the present invention provides a method of treating a subject suffering from a psychiatric disorder, comprising administering to the subject a therapeutically effective amount of a compound of formula I.

In an embodiment (E21) of any of the embodiments (E1) to (E15) the present invention provides a method of treating a subject suffering from a drug addiction, such as an alcohol, amphetamine, cocaine, or opiate addiction.

In an embodiment (E22) the present invention relates to compounds of formula I:

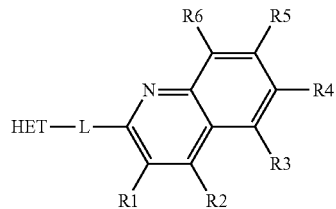

wherein R1-R6 and HET are as described in any of the previous embodiments (E1) to (E14) and -L- is a linker selected from —S—$CH_2$—, —$CH_2$—S— and —C≡C—.

Definition of Substitutents

As used in the context of the present invention, the terms "halo" and "halogen" are used interchangeably and refer to fluorine, chlorine, bromine or iodine.

The term "$C_1$-$C_6$ alkyl" refers to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl. The expression "$C_1$-$C_6$ hydroxyalkyl" refers to a $C_1$-$C_6$ alkyl group as defined above which is substituted with one hydroxy group. The term "halo($C_1$-$C_6$)alkyl" refers to a $C_1$-$C_6$ alkyl group as defined above which is substituted with up to three halogen atoms, such as trifluoromethyl.

The expression "$C_1$-$C_6$ alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methyl-pentoxy and n-hexyloxy. The alkoxy may optionally be substituted with up to three halogen atoms, such as trifluoromethoxy.

The term "$C_3$-$C_8$ cycloalkyl" typically refers to cyclopropyl, cyclobutyl, cyclopentyl, cyclohexyl, cycloheptyl or cyclooctyl. The expression "$C_1$-$C_6$ alkyl($C_3$-$C_8$)cycloalkyl" refers to a $C_3$-$C_8$ cycloalkyl as defined above which is substituted with a straight-chain or branched $C_1$-$C_6$ alkyl. Examples of such groups include, but are not limited to, cyclopropylmethyl.

The term "heterocycloalkyl" refers to a four to eight membered ring containing carbon atoms and up to three N, O or S atoms, provided that the four to eight membered ring does not contain adjacent O or adjacent S atoms. The open valency is on either the heteroatom or carbon atom. Examples of such groups include, but are not limited to, azetidinyl, oxetanyl, piperazinyl, morpholinyl, thiomorpholinyl and [1,4]diazepanyl. The term "hydroxyheterocycloalkyl" refers to a heterocycloalkyl as defined above which is substituted with one hydroxy group. The term "$C_1$-$C_6$ alkyl-heterocycloalkyl" refers to a heterocycloalkyl as defined above which is substituted with a $C_1$-$C_6$ alkyl group. Examples of such groups include, but are not limited to, tetrahydropyran-4-yl-methyl and 2-morpholin-4-yl-ethyl.

The term "aryl" refers to a phenyl ring, optionally substituted with halogen, $C_1$-$C_6$ alkyl, $C_1$-$C_6$ alkoxy or halo($C_1$-$C_6$) alkyl as defined above. Examples of such groups include, but are not limited to, phenyl and 4-chlorophenyl.

The term "$C_1$-$C_6$arylalkyl" refers to an aryl as defined above which is substituted with a straight-chain or branched $C_1$-$C_6$ alkyl. Examples of such groups include, but are not limited to, benzyl and 4-chlorobenzyl.

In a further embodiment one or more of the hydrogen atoms of the compound of formula I have been substituted by deuterium.

In the context of this application is should be understood that the meaning of "R1-R6", "R1 to R6" and "R1, R2, R3, R4, R5 and R6" is the same.

Additionally, the present invention further provides certain embodiments of the invention, that are described below.

In separate embodiments of the invention, the compound of formula I is selected among the following specific compounds listed in Table 1, in the form of the free base, one or more tautomers thereof or a pharmaceutically acceptable salt thereof. Table 1 lists compounds of the invention and the corresponding $IC_{50}$ values determined as described in the section "PDE10A inhibition assay". Each of the compounds constitutes an individual embodiment, of the present invention.

It should be understood that the various aspects, embodiments, implementations and features of the invention mentioned herein may be claimed separately, or in any combination, as illustrated by the following non-limiting examples.

TABLE 1

Compounds of the invention and $IC_{50}$ values

| Compound | IC50 (nM) |
|---|---|
| 2-[(E)-2-(5,7-Dimethyl-imidazo[1,2-a]pyrimidin-2-yl)-vinyl]-quinoline | 320 |
| 2-[(Z)-2-(5,7-Dimethyl-imidazo[1,2-a]pyrimidin-2-yl)-vinyl]-quinoline | 240 |
| 2-[2-(5,7-Dimethyl-imidazo[1,2-a]pyrimidin-2-yl)-ethyl]-quinoline | 310 |
| 2-[2-(5,7-Dimethyl-[1,2,4]triazolo[1,5-a]pyrimidin-2-yl)-ethyl]-quinoline | 72 |
| 2-[2-(5,8-Dimethyl-[1,2,4]triazolo[1,5-a]pyrazin-2-yl)-ethyl]-quinoline | 19 |
| 2-[2-(5,8-Dimethyl-[1,2,4]triazolo[1,5-a]pyrazin-2-yl)-ethyl]-quinoline | 7,4 |
| 2-[2-(5,7-Dimethyl-[1,2,4]triazolo[1,5-a]pyrimidin-2-yl)-ethyl]-6-methoxy-quinoline | 170 |
| 2-[2-(8-Methoxy-5-methyl-[1,2,4]triazolo[1,5-a]pyridin-2-yl)-ethyl]-quinoline | 12 |
| 2-[2-(8-Ethyl-5-methyl-[1,2,4]triazolo[1,5-a]pyridin-2-yl)-ethyl]-6-fluoro-quinoline | 25 |
| 6-Fluoro-2-[2-(8-methoxy-5-methyl-[1,2,4]triazolo[1,5-a]pyridin-2-yl)-ethyl]-quinoline | 34 |
| 2-[2-(5,8-Dimethyl-[1,2,4]triazolo[1,5-a]pyridin-2-yl)-ethyl]-quinoline | 24 |
| 2-[2-(6-Fluoro-quinolin-2-yl)-ethyl]-5-methyl-[1,2,4]triazolo[1,5-a]pyridin-8-ol | 85 |
| 2-[2-(5,8-Dimethyl-[1,2,4]triazolo[1,5-a]pyrazin-2-yl)-ethyl]-4-methyl-quinoline | 18 |
| 2-[2-(5,8-Dimethyl-[1,2,4]triazolo[1,5-a]pyrazin-2-yl)-ethyl]-4-methoxy-quinoline | 12 |
| 4-Methoxy-2-[2-(5-methyl-[1,2,4]triazolo[1,5-a]pyridin-2-yl)-ethyl]-quinoline | 190 |
| 4-Methoxy-2-[2-(8-methoxy-5-methyl-[1,2,4]triazolo[1,5-a]pyridin-2-yl)-ethyl]-quinoline | 35 |
| 4-Methyl-2-[2-(5-methyl-[1,2,4]triazolo[1,5-a]pyridin-2-yl)-ethyl]-quinoline | 140 |
| 2-[2-(8-Methoxy-5-methyl-[1,2,4]triazolo[1,5-a]pyridin-2-yl)-ethyl]-4-methyl-quinoline | 42 |
| 4-Chloro-8-fluoro-2-[(E)-2-(8-methoxy-5-methyl-[1,2,4]triazolo[1,5-a]pyridin-2-yl)-vinyl]-quinoline | 270 |
| 8-Fluoro-2-[2-(8-methoxy-5-methyl-[1,2,4]triazolo[1,5-a]pyridin-2-yl)-ethyl]-quinoline | 150 |
| 2-[2-(5,8-Dimethyl-[1,2,4]triazolo[1,5-a]pyrazin-2-yl)-ethyl]-7-fluoro-quinoline | 15 |
| 2-[2-(5,8-Dimethyl-[1,2,4]triazolo[1,5-a]pyrazin-2-yl)-ethyl]-6-fluoro-quinoline | 24 |
| 2-[2-(5,8-Dimethyl-[1,2,4]triazolo[1,5-a]pyrazin-2-yl)-ethyl]-6-fluoro-quinoline | 26 |
| 2-[2-(5,8-Dimethyl-[1,2,4]triazolo[1,5-a]pyrazin-2-yl)-ethyl]-4-fluoro-quinoline | 28 |
| 2-[(E)-2-(5,8-Dimethyl-[1,2,4]triazolo[1,5-a]pyrazin-2-yl)-vinyl]-6-fluoro-quinoline | 190 |
| 2-[2-(5,8-Dimethyl-[1,2,4]triazolo[1,5-a]pyrazin-2-yl)-ethyl]-7-fluoro-4-methoxy-quinoline | 26 |
| 2-[2-(5,8-Dimethyl-[1,2,4]triazolo[1,5-a]pyrazin-2-yl)-ethyl]-7-fluoro-quinolin-4-ol | 500 |
| 2-[(E)-2-(5,8-Dimethyl-[1,2,4]triazolo[1,5-a]pyrazin-2-yl)-vinyl]-7-trifluoromethyl-quinoline | 550 |
| 2-[2-(5,8-Dimethyl-[1,2,4]triazolo[1,5-a]pyrazin-2-yl)-ethyl]-6-fluoro-4-methoxy-quinoline | 14 |
| 2-[2-(5,8-Dimethyl-[1,2,4]triazolo[1,5-a]pyrazin-2-yl)-ethyl]-7-trifluoromethyl-quinoline | 240 |
| 2-[2-(5,8-Dimethyl-[1,2,4]triazolo[1,5-a]pyrazin-2-yl)-ethyl]-6-fluoro-quinolin-4-ol | 410 |
| 2-[2-(5,8-Dimethyl-[1,2,4]triazolo[1,5-a]pyrazin-2-yl)-ethyl]-5-fluoro-quinoline | 120 |
| 7-Chloro-2-[2-(5,8-dimethyl-[1,2,4]triazolo[1,5-a]pyrazin-2-yl)-ethyl]-quinoline | 52 |
| 2-[2-(5,8-Dimethyl-[1,2,4]triazolo[1,5-c]pyrimidin-2-yl)-ethyl]-6-isopropyl-quinoline | 61 |
| 2-[2-(5,8-Dimethyl-[1,2,4]triazolo[1,5-a]pyrazin-2-yl)-ethyl]-5,7-difluoro-quinoline | 110 |
| 2-[2-(5,8-Dimethyl-[1,2,4]triazolo[1,5-a]pyrazin-2-yl)-ethyl]-5,6,8-trifluoro-quinoline | 360 |
| 2-[2-(5,8-Dimethyl-[1,2,4]triazolo[1,5-a]pyrazin-2-yl)-ethyl]-6,8-difluoro-quinoline | 300 |
| 6-[2-(5,8-Dimethyl-[1,2,4]triazolo[1,5-a]pyrazin-2-yl)-ethyl]-[1,3]dioxolo[4,5-g]quinoline | 13 |
| 2-[2-(5,8-Dimethyl-[1,2,4]triazolo[1,5-a]pyrazin-2-yl)-ethyl]-6-fluoro-8-methyl-quinoline | 2000 |
| 2-[2-(5,8-Dimethyl-[1,2,4]triazolo[1,5-a]pyrazin-2-yl)-ethyl]-6-fluoro-7-methyl-quinoline | 8,8 |
| 6-[2-(5,8-Dimethyl-[1,2,4]triazolo[1,5-a]pyrazin-2-yl)-ethyl]-2,2-difluoro-[1,3]dioxolo[4,5-g]quinoline | 520 |
| 7-Chloro-2-[2-(5,8-dimethyl-[1,2,4]triazolo[1,5-a]pyrazin-2-yl)-ethyl]-quinoline-6-carbonitrile | 59 |
| 7-(5,8-Dimethyl-[1,2,4]triazolo[1,5-a]pyrazin-2-yl)-2,3-dihydro-[1,4]dioxino[2,3-g]quinoline | 4 |
| 6-Chloro-2-[2-(5,8-dimethyl-[1,2,4]triazolo[1,5-a]pyrazin-2-yl)-ethyl]-quinoline | 42 |
| 6-Chloro-2-[2-(5,8-dimethyl-[1,2,4]triazolo[1,5-a]pyrazin-2-yl)-ethyl]-8-fluoro-quinoline | 240 |
| 8-Chloro-2-[2-(5,8-dimethyl-[1,2,4]triazolo[1,5-a]pyrazin-2-yl)-ethyl]-6-methyl-quinoline | 290 |
| 5,7-Dichloro-2-[2-(5,8-dimethyl-[1,2,4]triazolo[1,5-a]pyrazin-2-yl)-ethyl]-quinoline | 39 |
| 2-[(E)-2-(5,8-Dimethyl-[1,2,4]triazolo[1,5-a]pyrazin-2-yl)-vinyl]-6-trifluoromethoxy-quinoline | 2800 |
| 2-[(E)-2-(5,8-Dimethyl-[1,2,4]triazolo[1,5-a]pyrazin-2-yl)-vinyl]-6-trifluoromethyl-quinoline | 490 |
| 2-[(E)-2-(5,8-Dimethyl-[1,2,4]triazolo[1,5-a]pyrazin-2-yl)-vinyl]-6-cyano-quinoline | 2100 |
| 2-[(E)-2-(5,8-Dimethyl-[1,2,4]triazolo[1,5-a]pyrazin-2-yl)-vinyl]-7-methoxy-quinoline | 13 |
| 2-[(E)-2-(5,8-Dimethyl-[1,2,4]triazolo[1,5-a]pyrazin-2-yl)-vinyl]-5-methoxy-quinoline | 19 |

In a particular embodiment of the present invention the compounds of the present invention have an $IC_{50}$ value of less than 50 nM, such as in the range of 0.2-20 nM, particularly in the range of 0.2-10 nM, such as in the range of 0.2-5 nM.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Compositions

The present invention further provides a pharmaceutical composition comprising a therapeutically effective amount of a compound of formula I and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of formula I and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound having the utility of a free base. When a compound of formula I contains a free base such salts are prepared in a conventional manner by treating a solution or suspension of a free base of formula I with a molar equivalent of a pharmaceutically acceptable acid. Representative examples of suitable organic and inorganic acids are described above.

For parenteral administration, solutions of the compounds of formula I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula I may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, *acacia*, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula I and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Therapeutically Effective Amount

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

Treatment of Disorders

As mentioned above, the compounds of formula I are PDE10A enzyme inhibitors and as such are useful to treat associated neurological and psychiatric disorders.

The invention thus provides a compound of formula I or a pharmaceutically acceptable acid addition salt thereof, as well as a pharmaceutical composition containing such a compound, for use in the treatment of a neurodegenerative disorder, psychiatric disorder or drug addiction in humans.

In one embodiment of the present invention, the neurodegenerative disorder or condition involves neurodegeneration of striatal medium spiny neurons in a human. In a specific embodiment of the present invention, the neurodegenerative disorder or condition is Huntington's disease. In a further embodiment the disorder is dyskinesia associated with dopamine agonist therapy.

In an embodiment the psychiatric disorder is selected from the group consisting of schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type.

This invention further provides a method of treating a drug addiction, for example an alcohol, amphetamine, cocaine, or opiate addiction, in a human, which method comprises administering to said human an amount of a compound of formula I effective in treating addiction, such as drug addiction.

The term "drug addiction", as used herein, means an abnormal desire for a drug and is generally characterized by motivational disturbances such a compulsion to take the desired drug and episodes of intense drug craving.

Other disorders that can be treated according to the present invention are obsessive/compulsive disorders, non-insuline demanding diabetes mellitus (NIDDM), and Tourette's syndrome and other tic disorders as well as Attention Deficit/Hyperactivity Disorder (ADHD).

The compounds of formula I or pharmaceutically acceptable salts thereof may be used in combination with one or more other drugs (including typical and atypical antpsychotic agent) in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. The combinations, uses and methods of treatment of the invention may also provide advantages in treatment of patients who fail to respond adequately or who are resistant to other known treatments.

Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The term "neuroleptic agent" as used herein refers to drugs, which have the effect on cognition and behaviour of antipsychotic agent drugs that reduce confusion, delusions, hallucinations, and psychomotor agitation in patients with psychoses. Also known as major tranquilizers and antipsychotic drugs, neuroleptic agents include, but are not limited to: typical antipsychotic drugs, including phenothiazines, further divided into the aliphatics, piperidines, and piperazines, thioxanthenes (e.g., cisordinol), butyrophenones (e.g., haloperidol), dibenzoxazepines (e.g., loxapine), dihydroindolones (e.g., molindone), diphenylbutylpiperidines (e.g., pimozide), and atypical antipsychotic drugs, including benzisoxazoles (e.g., risperidone), sertindole, olanzapine, quetiapine, osanetant and ziprasidone.

Particularly preferred neuroleptic agents for use in the invention are sertindole, olanzapine, risperidone, quetiapine, aripiprazole, haloperidol, clozapine, ziprasidone and osanetant.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

The invention disclosed herein is further illustrated by the following non-limiting examples.

Experimental Section
Preparation of the Compounds of the Invention

Compounds of the general formula I of the invention may be prepared as described in the following reaction schemes.

Compounds of formula I, wherein L is —CH=CH— or —CH$_2$—CH$_2$— can be prepared by the reaction sequence shown in scheme 1.

Specifically, compounds of formula I, wherein L is —CH$_2$—CH$_2$— can be prepared by reduction of an alkene of formula I, wherein L is —CH=CH—, by hydrogenation using a transition metal catalyst, such as palladium metal, together with a hydrogen source, such as hydrogen gas, ammonium hydrogen carbonate, or cyclohexadiene. Said alkenes of formula I, wherein L is —CH=CH— can be prepared by the Wittig reaction between a phosphonium salt of formula IV and an aldehyde of formula V in a suitable solvent, such as tetrahydrofuran, in the presence of a suitable base, such as 1,8-diazabicyclo[5.4.0]undec-7-ene. Phosphonium salts of formula IV are readily available by reaction of compounds of formula IV (see scheme 1 above) with triphenylphosphine by methods known to chemists skilled in the art and as described in e.g. WO-2011072696, WO-2011072694 and WO-2009152825. Aldehydes of formula V are commercially available or available by methods described in the literature see e.g. Organometallics (2011), 30(5), 1008-1012, Journal of Medicinal Chemistry (2010), 53(24), 8663-8678. Chemical Communications (2010), 46(35), 6554-6556, Journal of Medicinal Chemistry (2010), 53(5), Science of Synthesis (2005), 15 389-549. Journal of the Chemical Society (1932), Journal of the American Chemical Society (1941), 63 2654-5.

General Methods
Analytical LC-MS Data were Obtained Using the Following Method:
Method 111:

LC-MS were run on a Sciex API150EX equipped with APPI-source operating in positive ion mode. The HPLC consisted of Shimadzu LC10-ADvp LC pumps. SPD-M20A PDA UV-detector (operating at 254 nM) and shimadzu CBM-20A system controller. Autosampler was Gilson 215. Colomn oven was a Metalox model 200-C and column temperature: 60° C. injector: Gilson model 841 (1 microliter loop). ELS detector was a Sedere Sedex 85.

LC-conditions: The column was a Waters Symmetry C-18. 4.6×30 mm. 3.5 µm operating at 60° C. with 3.3 ml/min of a binary gradient consisting of Solvent A: 100% H2O 0.05% TFA and Solvent B: 95% ACN 5% H2O 0.035% TFA
Injection vol: 10 µl (1 µl injected on the column)
Gradient: 10% B to 100% B in 2.4 min
10% B in 0.4 min.
Total run time: 2.8 min

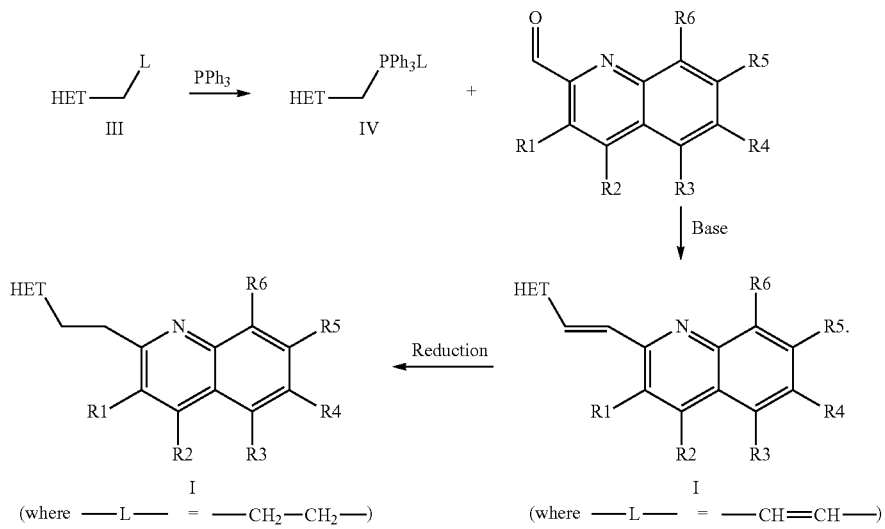

Scheme 1

Method 131:

LC-MS were run on a Sciex API150EX equipped with APPI-source operating in positive ion mode. The HPLC consisted of Shimadzu LC10-ADvp LC pumps. SPD-M20A PDA UV-detector (operating at 254 nM) and shimadzu CBM-20A system controller. Autosampler was Gilson 215. Colomn oven was a Jones Chromatography 7990R and column temperature: 60° C.

ELS detector was a Sedere Sedex 85.

LC-conditions: The column was a Waters Symmetry C-18. 4.6×30 mm. 3.5 µm operating at 60° C. with 3.0 ml/min of a binary gradient consisting of Solvent A: H2O with 0.05% v/v TFA and Solvent B: Methanol with 0.05% TFA Injection vol: 10 µl (1 µl injected on the column)
Gradient:
0.01 min 17% B (v/v)
0.27 min 28% B (v/v)
0.53 min 39% B (v/v)
0.80 min 50% B (v/v)
1.07 min 59% B (v/v)
1.34 min 68% B (v/v)
1.60 min 78% B (v/v)
1.87 min 86% B (v/v)
2.14 min 93% B (v/v)
2.38 min 100% B (v/v)
2.40 min 17% B (v/v)
2.80 min 17% B (v/v)
Total run time: 2.8 min
Method 132

LC-MS were run on a Sciex API150EX equipped with APPI-source operating in positive ion mode. The HPLC consisted of Shimadzu LC10-ADvp LC pumps. SPD-M20A PDA detector (operating at 254 nM) and SCL-10A system controller. Autosampler was Gilson 215. Colomn oven was a Jones Chromatography 7990R and ELS detector was a Sedere Sedex 85.

LC-conditions: The column was a Waters Symmetry C-18. 4.6×30 mm. 3.5 µoperating at 60° C. with 2.5 ml/min of a binary gradient consisting of water+0.05% TFA (A) and methanol+0.05% TFA (B).
Gradient: 0.01 min. 5% B
  2.38 min. 100% B
  2.40 min. 5% B
  2.80 min. 5% B
Total run time: 2.8 minutes
Method 350

LC-MS were run on a Sciex API300 equipped with APPI source operating in positive ion mode. The UPLC consisted of Waters Aquity including column manager. binary solvent manager. sample organizer. PDA detector (operating at 254 nM) and ELS detector.

LC-conditions: The column was a Waters Aquity UPLC BEH C-18. 2.1×50 mm. 1.7 µm operating at 60° C. with 1.2 ml/min of a binary gradient consisting of water+0.05% TFA (A) and 95% acetonitrile containing 5% water+0.03% TFA (B).

| Gradient: | Time (min.) | % B |
|---|---|---|
| | 0.00 | 10.0 |
| | 1.00 | 100.0 |
| | 1.01 | 10.0 |
| | 1.15 | 10.0 |
| Total run time 1.15 min | | |

Preparative LC-MS-purification was performed on a PE Sciex API 150EX instrument with atmospheric pressure chemical ionization. Column: 50×20 mm YMC ODS-A with 5 micro m particle size; Method: Linear gradient elution with A:B=80:20 to 0:100 in 7 minutes and with a flow rate of 22.7 mL/minute. Fraction collection was performed by split-flow MS detection.

$^1$H NMR spectra were recorded at 500.13 MHz on a Bruker Avance AV500 instrument or at 600.16 MHz on a Bruker Avance Ultrashield plus instrument. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, td=triplet of doublets, tt=triplet of triplets, m=multiplet, br s=broad singlet and br=broad signal.

Abbreviations are in accordance with to the ACS Style Guide: "The ACS Styleguide—A manual for authors and editors" Janet S. Dodd, Ed. 1997, ISBN: 0841234620

Preparation of Intermediates

Phosphonium salts of formula IV shown in scheme 1 are readily available by reaction of compounds of formula IV (see scheme 1 above) with triphenylphosphine by methods known to chemists skilled in the art and as described in e.g. WO-2011072696, WO-2011072694 and WO-2009152825. Aldehydes of formula V are commercially available or available by methods described in the literature see e.g. Organometallics (2011), 30(5), 1008-1012, Journal of Medicinal Chemistry (2010), 53(24), 8663-8678. Chemical Communications (2010), 46(35), 6554-6556, Journal of Medicinal Chemistry (2010), 53(5), Science of Synthesis (2005), 15 389-549. Journal of the Chemical Society (1932), Journal of the American Chemical Society (1941), 63 2654-5.

2-[(E)-2-(5,8-Dimethyl-[1,2,4]triazolo[1,5-a]pyrazin-2-yl)-vinyl]-quinoline-6-carbonitrile

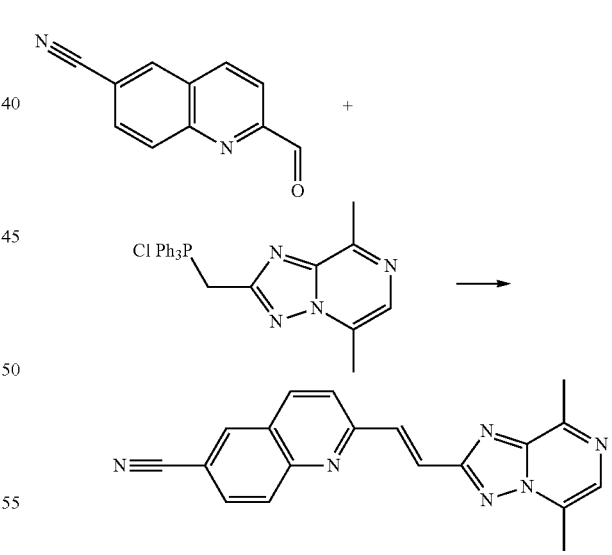

To a suspension of (5,8-Dimethyl-[1,2,4]triazolo[1,5-a]pyrazin-2-ylmethyl)-triphenyl-phosphonium; chloride (0.222 g, 0.483 mmol) and 2-Formyl-quinoline-6-carbonitrile (80 mg, 0.4 mmol) in dry Tetrahydrofuran (6 mL, 80 mmol) was added 1,8-Diazabicyclo[5.4.0]undec-7-ene (66 uL, 0.44 mmol) (reaction mixture turns slightly yellow for a while and precipitation changes character) and the mixture was stirred at room temperature under an atmosphere of Argon overnight. The mixture was rotovaped and the THF was evaporated off. The solid was dissolved in DCM and was chromatographed on silicagel (0-30% MeOH in EtOAc). Pure product 2-[(E)-2-(5,8-Dimethyl-[1,2,4]triazolo[1,5-a]pyrazin-2-yl)-vinyl]-quinoline-6-carbonitrile precipitates in one of the fractions (10): isolated by filtration. Yield: 6 mg white solid.

The following intermediates were made in a similar way:
2-[2-(5,7-Dimethyl-imidazo[1,2-a]pyrimidin-2-yl)-vinyl]-quinoline
2-[2-(5,7-Dimethyl-[1,2,4]triazolo[1,5-a]pyrimidin-2-yl)-vinyl]-quinoline
2-[2-(5,8-Dimethyl-[1,2,4]triazolo[1,5-a]pyrazin-2-yl)-vinyl]-quinoline
2-[2-(5,8-Dimethyl-[1,2,4]triazolo[1,5-a]pyrazin-2-yl)-vinyl]-quinoline
2-[2-(5,7-Dimethyl-[1,2,4]triazolo[1,5-a]pyrimidin-2-yl)-vinyl]-6-methoxy-quinoline
2-[2-(8-Methoxy-5-methyl-[1,2,4]triazolo[1,5-a]pyridin-2-yl)-vinyl]-quinoline
2-[2-(8-Ethyl-5-methyl-[1,2,4]triazolo[1,5-a]pyridin-2-yl)-vinyl]-6-fluoro-quinoline
6-Fluoro-2-[2-(8-methoxy-5-methyl-[1,2,4]triazolo[1,5-a]pyridin-2-yl)-vinyl]-quinoline
2-[2-(5,8-Dimethyl-[1,2,4]triazolo[1,5-a]pyridin-2-yl)-vinyl]-quinoline
2-[2-(6-Fluoro-quinolin-2-yl)-vinyl]-5-methyl-[1,2,4]triazolo[1,5-a]pyridin-8-ol
2-[2-(5,8-Dimethyl-[1,2,4]triazolo[1,5-a]pyrazin-2-yl)-vinyl]-4-methyl-quinoline
2-[2-(5,8-Dimethyl-[1,2,4]triazolo[1,5-a]pyrazin-2-yl)-vinyl]-4-methoxy-quinoline
4-Methoxy-2-[2-(5-methyl-[1,2,4]triazolo[1,5-a]pyridin-2-yl)-vinyl]-quinoline
4-Methoxy-2-[2-(8-methoxy-5-methyl-[1,2,4]triazolo[1,5-a]pyridin-2-yl)-vinyl]-quinoline
4-Methyl-2-[2-(5-methyl-[1,2,4]triazolo[1,5-a]pyridin-2-yl)-vinyl]-quinoline
2-[2-(8-Methoxy-5-methyl-[1,2,4]triazolo[1,5-a]pyridin-2-yl)-vinyl]-4-methyl-quinoline
4-Chloro-8-fluoro-2-[(E)-2-(8-methoxy-5-methyl-[1,2,4]triazolo[1,5-a]pyridin-2-yl)-vinyl]-quinoline
8-Fluoro-2-[2-(8-methoxy-5-methyl-[1,2,4]triazolo[1,5-a]pyridin-2-yl)-vinyl]-quinoline
2-[2-(5,8-Dimethyl-[1,2,4]triazolo[1,5-a]pyrazin-2-yl)-vinyl]-7-fluoro-quinoline
2-[2-(5,8-Dimethyl-[1,2,4]triazolo[1,5-a]pyrazin-2-yl)-vinyl]-6-fluoro-quinoline
2-[2-(5,8-Dimethyl-[1,2,4]triazolo[1,5-a]pyrazin-2-yl)-vinyl]-6-fluoro-quinoline
2-[2-(5,8-Dimethyl-[1,2,4]triazolo[1,5-a]pyrazin-2-yl)-vinyl]-4-fluoro-quinoline
2-[(E)-2-(5,8-Dimethyl-[1,2,4]triazolo[1,5-a]pyrazin-2-yl)-vinyl]-6-fluoro-quinoline
2-[2-(5,8-Dimethyl-[1,2,4]triazolo[1,5-a]pyrazin-2-yl)-vinyl]-7-fluoro-4-methoxy-quinoline
2-[2-(5,8-Dimethyl-[1,2,4]triazolo[1,5-a]pyrazin-2-yl)-vinyl]-7-fluoro-quinolin-4-ol
2-[(E)-2-(5,8-Dimethyl-[1,2,4]triazolo[1,5-a]pyrazin-2-yl)-vinyl]-7-trifluoromethyl-quinoline
2-[2-(5,8-Dimethyl-[1,2,4]triazolo[1,5-a]pyrazin-2-yl)-vinyl]-6-fluoro-4-methoxy-quinoline
2-[2-(5,8-Dimethyl-[1,2,4]triazolo[1,5-a]pyrazin-2-yl)-vinyl]-7-trifluoromethyl-quinoline
2-[2-(5,8-Dimethyl-[1,2,4]triazolo[1,5-a]pyrazin-2-yl)-vinyl]-6-fluoro-quinolin-4-ol
2-[2-(5,8-Dimethyl-[1,2,4]triazolo[1,5-a]pyrazin-2-yl)-vinyl]-5-fluoro-quinoline
7-Chloro-2-[2-(5,8-dimethyl-[1,2,4]triazolo[1,5-a]pyrazin-2-yl)-vinyl]-quinoline
2-[2-(5,8-Dimethyl-[1,2,4]triazolo[1,5-c]pyrimidin-2-yl)-vinyl]-6-isopropyl-quinoline
2-[2-(5,8-Dimethyl-[1,2,4]triazolo[1,5-a]pyrazin-2-yl)-vinyl]-5,7-difluoro-quinoline
2-[2-(5,8-Dimethyl-[1,2,4]triazolo[1,5-a]pyrazin-2-yl)-vinyl]-5,6,8-trifluoro-quinoline
2-[2-(5,8-Dimethyl-[1,2,4]triazolo[1,5-a]pyrazin-2-yl)-vinyl]-6,8-difluoro-quinoline
6-[2-(5,8-Dimethyl-[1,2,4]triazolo[1,5-a]pyrazin-2-yl)-vinyl]-[1,3]dioxolo[4,5-g]quinoline
2-[2-(5,8-Dimethyl-[1,2,4]triazolo[1,5-a]pyrazin-2-yl)-vinyl]-6-fluoro-8-methyl-quinoline
2-[2-(5,8-Dimethyl-[1,2,4]triazolo[1,5-a]pyrazin-2-yl)-vinyl]-6-fluoro-7-methyl-quinoline
6-[2-(5,8-Dimethyl-[1,2,4]triazolo[1,5-a]pyrazin-2-yl)-vinyl]-2,2-difluoro-[1,3]dioxolo[4,5-g]quinoline
7-Chloro-2-[2-(5,8-dimethyl-[1,2,4]triazolo[1,5-a]pyrazin-2-yl)-vinyl]-quinoline-6-carbonitrile
7-[2-(5,8-Dimethyl-[1,2,4]triazolo[1,5-a]pyrazin-2-yl)-vinyl]-2,3-dihydro-[1,4]dioxino[2,3-g]quinoline
6-Chloro-2-[2-(5,8-dimethyl-[1,2,4]triazolo[1,5-a]pyrazin-2-yl)-vinyl]-quinoline
6-Chloro-2-[2-(5,8-dimethyl-[1,2,4]triazolo[1,5-a]pyrazin-2-yl)-vinyl]-8-fluoro-quinoline
8-Chloro-2-[2-(5,8-dimethyl-[1,2,4]triazolo[1,5-a]pyrazin-2-yl)-vinyl]-6-methyl-quinoline
5,7-Dichloro-2-[2-(5,8-dimethyl-[1,2,4]triazolo[1,5-a]pyrazin-2-yl)-vinyl]-quinoline Preparation of Compounds of the Invention Example 1

2-[(E)-2-(5,8-Dimethyl-[1,2,4]triazolo[1,5-a]pyrazin-2-yl)-vinyl]-6-trifluoromethyl-quinoline

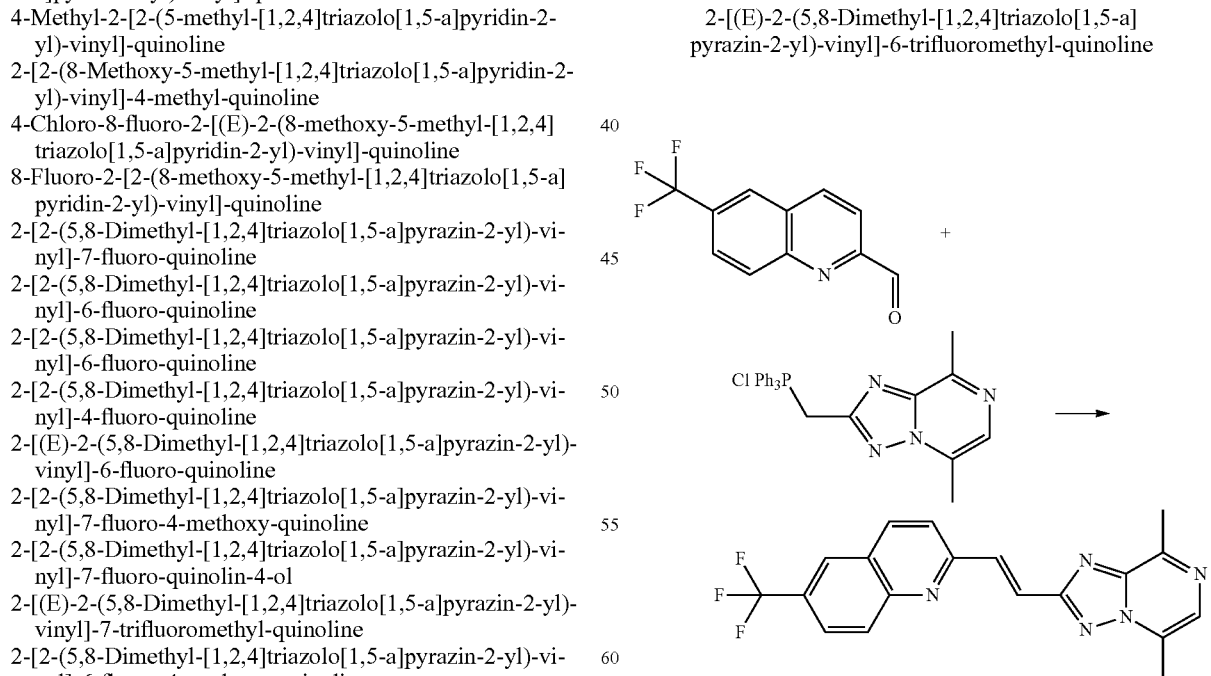

To a solution of (5,8-Dimethyl-[1,2,4]triazolo[1,5-a]pyrazin-2-ylmethyl)-triphenyl-phosphonium; chloride (0.48 g, 1.0 mmol) and 6-Trifluoromethyl-quinoline-2-carbaldehyde (0.24 g, 1.0 mmol) in dry N,N-Dimethylformamide (25 mL, 320 mmol) was added 1,8-Diazabicyclo[5.4.0]undec-7- ene (0.16 mL, 1.0 mmol) (reaction mixture turns more dark) and the mixture was stirred at room temperature under an atmosphere of Argon overnight. The reaction mixture shows precipitation the day after.

Precipitation filtered of. Washed with water and diethyl ether. Dried on filter by vacuum, then in vacuo for 2 hours at 60° C. Filtercake: Giving a white solid containing the final product 2-[(E)-2-(5,8-Dimethyl-[1,2,4]triazolo[1,5-a]pyrazin-2-yl)-vinyl]-6-trifluoromethyl-quinoline. LC-MS: m/z=369.7 (MH+). Rt=1.96 min., method=131.

The following compounds were made in a similar way:
2-[(E)-2-(5,7-Dimethyl-imidazo[1,2-a]pyrimidin-2-yl)-vinyl]-quinoline LC-MS: m/z=301.1 (MH+). Rt=0.55 min., method=111.
2-[(E)-2-(5,8-Dimethyl-[1,2,4]triazolo[1,5-a]pyrazin-2-yl)-vinyl]-6-trifluoromethoxy-quinoline LC-MS: m/z=386.1, Rt=1.97 min, method=131
2-[(E)-2-(5,8-Dimethyl-[1,2,4]triazolo[1,5-a]pyrazin-2-yl)-vinyl]-6-cyano-quinoline LC-MS: m/z=327.3, Rt=1.97 min, method=131
2-[(E)-2-(5,8-Dimethyl-[1,2,4]triazolo[1,5-a]pyrazin-2-yl)-vinyl]-7-methoxy-quinoline LC-MS: m/z=332.1, Rt=1.22 min, method=131
2-[(E)-2-(5,8-Dimethyl-[1,2,4]triazolo[1,5-a]pyrazin-2-yl)-vinyl]-5-methoxy-quinoline LC-MS: m/z=332.2, Rt=1.41 min, method=131

Example 2

6-[2-(5,8-Dimethyl-[1,2,4]triazolo[1,5-a]pyrazin-2-yl)-ethyl]-1,3-dioxolo[4,5-g]quinoline

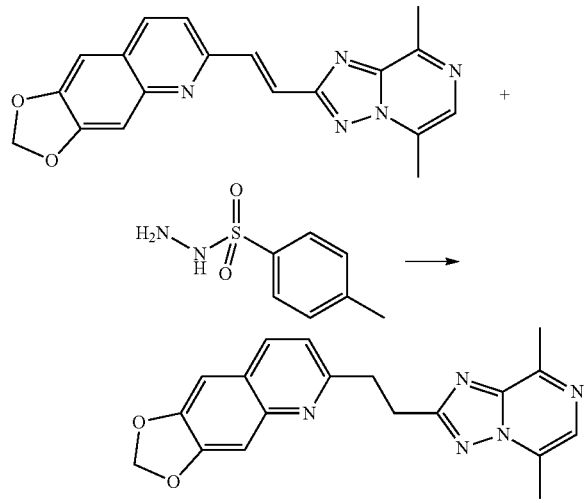

6-[(E)-2-(5,8-Dimethyl-[1,2,4]triazolo[1,5-a]pyrazin-2-yl)-vinyl]-1,3-dioxolo[4,5-g]quinoline (0.183 g, 0.530 mmol) was dissolved in N,N-Dimethylformamide (11 mL, 140 mmol). [B] p-Toluenesulfonylhydrazide (0.296 g, 1.59 mmol; Supplier=Avocado) was added and the reaction was stirred at 130° C. under an atmosphere of Argon ON. LCMS was done and showed almost complete conversion. 0.100 g [B] was added to the mixture was stirred 2 days at 130 C.

DMF was evaporated. The solid was dissolved in 50 mL EtOAc and extracted with 2×25 mL sat. NaHCO3 and washed with 50 mL brine. The organic phase was rotovaped and chromatographed on silicagel using EtOAc: heptane (1:1) and then 0-30% MeOH in EtOAc. Yield: 40 mg solid. LC-MS: m/z=348.4 (MH+). Rt=0.34 min., method=350.

The following compounds were prepared in a similar way:
2-[2-(5,7-Dimethyl-imidazo[1,2-a]pyrimidin-2-yl)-ethyl]-quinoline LC-MS: m/z=303.4 (MH+). Rt=0.34 min., method=111
2-[2-(5,7-Dimethyl-[1,2,4]triazolo[1,5-a]pyrimidin-2-yl)-ethyl]-quinoline LC-MS: m/z=304.3 (MH+). Rt=0.46 min., method=111
2-[2-(5,8-Dimethyl-[1,2,4]triazolo[1,5-a]pyrazin-2-yl)-ethyl]-quinoline LC-MS: m/z=304.3 (MH+). Rt=0.61 min., method=131
2-[2-(5,7-Dimethyl-[1,2,4]triazolo[1,5-a]pyrimidin-2-yl)-ethyl]-6-methoxy-quinoline LC-MS: m/z=334.5 (MH+). Rt=0.62 min., method=131
2-[2-(8-Methoxy-5-methyl-[1,2,4]triazolo[1,5-a]pyridin-2-yl)-ethyl]-quinoline LC-MS: m/z=319.1 (MH+). Rt=0.71 min., method=131
2-[2-(8-Ethyl-5-methyl-[1,2,4]triazolo[1,5-a]pyridin-2-yl)-ethyl]-6-fluoro-quinoline LC-MS: m/z=335.2 (MH+). Rt=1.12 min., method=131
6-Fluoro-2-[2-(8-methoxy-5-methyl-[1,2,4]triazolo[1,5-a]pyridin-2-yl)-ethyl]-quinoline LC-MS: m/z=337.5 (MH+). Rt=0.96 min., method=131
2-[2-(5,8-Dimethyl-[1,2,4]triazolo[1,5-a]pyridin-2-yl)-ethyl]-quinoline LC-MS: m/z=303.5 (MH+). Rt=0.76 min., method=131
2-[2-(6-Fluoro-quinolin-2-yl)-ethyl]-5-methyl-[1,2,4]triazolo[1,5-a]pyridin-8-ol LC-MS: m/z=323.1 (MH+). Rt=0.41 min., method=350
2-[2-(5,8-Dimethyl-[1,2,4]triazolo[1,5-a]pyrazin-2-yl)-ethyl]-4-methyl-quinoline LC-MS: m/z=318.2 (MH+). Rt=0.83 min., method=131
2-[2-(5,8-Dimethyl-[1,2,4]triazolo[1,5-a]pyrazin-2-yl)-ethyl]-4-methoxy-quinoline LC-MS: m/z=334.5 (MH+). Rt=0.9 min., method=131
4-Methoxy-2-[2-(5-methyl-[1,2,4]triazolo[1,5-a]pyridin-2-yl)-ethyl]-quinoline LC-MS: m/z=319.2 (MH+). Rt=0.93 min., method=131
4-Methoxy-2-[2-(8-methoxy-5-methyl-[1,2,4]triazolo[1,5-a]pyridin-2-yl)-ethyl]-quinoline LC-MS: m/z=349.1 (MH+). Rt=1.01 min., method=131
4-Methyl-2-[2-(5-methyl-[1,2,4]triazolo[1,5-a]pyridin-2-yl)-ethyl]-quinoline LC-MS: m/z=303.4 (MH+). Rt=0.85 min., method=131
2-[2-(8-Methoxy-5-methyl-[1,2,4]triazolo[1,5-a]pyridin-2-yl)-ethyl]-4-methyl-quinoline LC-MS: m/z=333.2 (MH+). Rt=0.95 min., method=131
4-Chloro-8-fluoro-2-[(E)-2-(8-methoxy-5-methyl-[1,2,4]triazolo[1,5-a]pyridin-2-yl)-vinyl]-quinoline LC-MS: m/z=369.2 (MH+). Rt=1.98 min., method=131
8-Fluoro-2-[2-(8-methoxy-5-methyl-[1,2,4]triazolo[1,5-a]pyridin-2-yl)-ethyl]-quinoline LC-MS: m/z=337.5 (MH+). Rt=1.32 min., method=131
2-[2-(5,8-Dimethyl-[1,2,4]triazolo[1,5-a]pyrazin-2-yl)-ethyl]-7-fluoro-quinoline LC-MS: m/z=321.8 (MH+). Rt=0.43 min., method=350
2-[2-(5,8-Dimethyl-[1,2,4]triazolo[1,5-a]pyrazin-2-yl)-ethyl]-6-fluoro-quinoline LC-MS: m/z=322.1 (MH+). Rt=0.44 min., method=350
2-[2-(5,8-Dimethyl-[1,2,4]triazolo[1,5-a]pyrazin-2-yl)-ethyl]-4-fluoro-quinoline LC-MS: m/z=321.9 (MH+). Rt=0.44 min., method=350
2-[2-(5,8-Dimethyl-[1,2,4]triazolo[1,5-a]pyrazin-2-yl)-ethyl]-7-fluoro-4-methoxy-quinoline LC-MS: m/z=352.3 (MH+). Rt=0.87 min., method=131

2-[2-(5,8-Dimethyl-[1,2,4]triazolo[1,5-a]pyrazin-2-yl)-ethyl]-7-fluoro-quinolin-4-ol LC-MS: m/z=338.4 (MH+). Rt=1.08 min., method=131

2-[(E)-2-(5,8-Dimethyl-[1,2,4]triazolo[1,5-a]pyrazin-2-yl)-vinyl]-7-trifluoromethyl-quinoline LC-MS: m/z=370.2 (MH+). Rt=0.79 min., method=350

2-[2-(5,8-Dimethyl-[1,2,4]triazolo[1,5-a]pyrazin-2-yl)-ethyl]-6-fluoro-4-methoxy-quinoline LC-MS: m/z=352.3 (MH+). Rt=0.9 min., method=131

2-[2-(5,8-Dimethyl-[1,2,4]triazolo[1,5-a]pyrazin-2-yl)-ethyl]-7-trifluoromethyl-quinoline LC-MS: m/z=372.3 (MH+). Rt=0.61 min., method=350

2-[2-(5,8-Dimethyl-[1,2,4]triazolo[1,5-a]pyrazin-2-yl)-ethyl]-6-fluoro-quinolin-4-ol LC-MS: m/z=338.1 (MH+). Rt=1.05 min., method=131

2-[2-(5,8-Dimethyl-[1,2,4]triazolo[1,5-a]pyrazin-2-yl)-ethyl]-5-fluoro-quinoline LC-MS: m/z=322.1 (MH+). Rt=1.25 min., method=131

7-Chloro-2-[2-(5,8-dimethyl-[1,2,4]triazolo[1,5-a]pyrazin-2-yl)-ethyl]-quinoline LC-MS: m/z=338.3 (MH+). Rt=1.82 min., method=132

2-[2-(5,8-Dimethyl-[1,2,4]triazolo[1,5-c]pyrimidin-2-yl)-ethyl]-6-isopropyl-quinoline LC-MS: m/z=346.2 (MH+). Rt=0.47 min., method=350

2-[2-(5,8-Dimethyl-[1,2,4]triazolo[1,5-a]pyrazin-2-yl)-ethyl]-5,7-difluoro-quinoline LC-MS: m/z=339.8 (MH+). Rt=0.57 min., method=350

2-[2-(5,8-Dimethyl-[1,2,4]triazolo[1,5-a]pyrazin-2-yl)-ethyl]-5,6,8-trifluoro-quinoline LC-MS: m/z=358.4 (MH+). Rt=0.67 min., method=350

2-[2-(5,8-Dimethyl-[1,2,4]triazolo[1,5-a]pyrazin-2-yl)-ethyl]-6,8-difluoro-quinoline LC-MS: m/z=339.7 (MH+). Rt=0.6 min., method=350

6-[2-(5,8-Dimethyl-[1,2,4]triazolo[1,5-a]pyrazin-2-yl)-ethyl]-[1,3]dioxolo[4,5-g]quinoline LC-MS: m/z=348.4 (MH+). Rt=0.34 min., method=350

2-[2-(5,8-Dimethyl-[1,2,4]triazolo[1,5-a]pyrazin-2-yl)-ethyl]-6-fluoro-8-methyl-quinoline LC-MS: m/z=336.3 (MH+). Rt=0.57 min., method=350

2-[2-(5,8-Dimethyl-[1,2,4]triazolo[1,5-a]pyrazin-2-yl)-ethyl]-6-fluoro-7-methyl-quinoline LC-MS: m/z=336.3 (MH+). Rt=0.41 min., method=350

6-[2-(5,8-Dimethyl-[1,2,4]triazolo[1,5-a]pyrazin-2-yl)-ethyl]-2,2-difluoro-[1,3]dioxolo[4,5-g]quinoline LC-MS: m/z=384.2 (MH+). Rt=1.6 min., method=131

7-Chloro-2-[2-(5,8-dimethyl-[1,2,4]triazolo[1,5-a]pyrazin-2-yl)-ethyl]-quinoline-6-carbonitrile LC-MS: m/z=363.2 (MH+). Rt=1.61 min., method=131

7-[2-(5,8-Dimethyl-[1,2,4]triazolo[1,5-a]pyrazin-2-yl)-ethyl]-2,3-dihydro-[1,4]dioxino[2,3-g]quinoline LC-MS: m/z=362.3 (MH+). Rt=0.82 min., method=131

6-Chloro-2-[2-(5,8-dimethyl-[1,2,4]triazolo[1,5-a]pyrazin-2-yl)-ethyl]-quinoline LC-MS: m/z=338.3 (MH+). Rt=1.31 min., method=131

6-Chloro-2-[2-(5,8-dimethyl-[1,2,4]triazolo[1,5-a]pyrazin-2-yl)-ethyl]-8-fluoro-quinoline LC-MS: m/z=356.2 (MH+). Rt=1.72 min., method=131

8-Chloro-2-[2-(5,8-dimethyl-[1,2,4]triazolo[1,5-a]pyrazin-2-yl)-ethyl]-6-methyl-quinoline LC-MS: m/z=352.4 (MH+). Rt=1.7 min., method=131

5,7-Dichloro-2-[2-(5,8-dimethyl-[1,2,4]triazolo[1,5-a]pyrazin-2-yl)-ethyl]-quinoline LC-MS: m/z=372.0 (MH+). Rt=2.01 min., method=131

Pharmacological Testing

PDE10A Enzyme

Active PDE10A enzyme is prepared in a number of ways for use in PDE assays (Loughney, K. et al. *Gene* 1999, 234, 109-117; Fujishige, K. et al. *Eur J Biochem.* 1999, 266, 1118-1127 and Soderling, S. et al. *Proc. Natl. Acad. Sci.* 1999, 96, 7071-7076). PDE10A can be expressed as full-length proteins or as truncated proteins, as long as they express the catalytic domain. PDE10A can be prepared in different cell types, for example insect cells or *E. coli*. An example of a method to obtain catalytically active PDE10A is as follows: The catalytic domain of human PDE10A (amino acids 440-779 from the sequence with accession number NP 006652) is amplified from total human brain total RNA by standard RT-PCR and is cloned into the BamH1 and Xho1 sites of the pET28a vector (Novagen). Expression in *coli* is performed according to standard protocols. Briefly, the expression plasmids are transformed into the BL21(DE3) *E. coli* strain, and 50 mL cultures inoculated with the cells allowed to grow to an OD600 of 0.4-0.6 before protein expression is induced with 0.5 mM IPTG. Following induction, the cells are incubated overnight at room temperature, after which the cells are collected by centrifugation. Cells expressing PDE10A are resuspended in 12 mL (50 mM TRIS-HCl-pH8.0, 1 mM $MgCl_2$ and protease inhibitors). The cells are lysed by sonication, and after all cells are lysed, TritonX100 is added according to Novagen protocols. PDE10A is partially purified on Q sepharose and the most active fractions were pooled.

PDE10A Inhibition Assay

A PDE10A assay may for example, be performed as follows: The assay is performed in 60 uL samples containing a fixed amount of the relevant PDE enzyme (sufficient to convert 20-25% of the cyclic nucleotide substrate), a buffer (50 mM HEPES7.6; 10 mM $MgCl_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and $IC_{50}$ values can be calculated using the XIfit extension to EXCEL.

Phencyclidine (PCP) Induced Hyperactivity

Male mice (NM RI, Charles River) weighing 20-25 g are used. Eight mice are used in each group receiving the test compound (5 mg/kg) plus PCP (2.3 mg/kg) including the parallel control groups receiving the vehicle of the test compound plus PCP or vehicle injections only. The injection volume is 10 ml/kg. The experiment is made in normal light conditions in an undisturbed room. The test substance is injected per oss 60 min before injection of PCP, which is administered subcutaneous. Immediately after injection of PCP the mice are placed individually in special designed test cage (20 cm×32 cm). The activity is measured by 5×8 infrared light sources and photocells spaced by 4 cm. The light beams cross the cage 1.8 cm above the bottom of the cage. Recording of a motility count requires interruption of adjacent light beams, thus avoiding counts induced by stationary movements of the mice.

Motility is recorded in 5 min intervals for a period of 1 hour. The drug effect is calculated on the total counts during the 1 hour behavioral test period in the following manner:

The mean motility induced by vehicle treatment in the absence of PCP is used as baseline. The 100 per cent effect of PCP is accordingly calculated to be total motility counts minus baseline. The response in groups receiving test compound is thus determined by the total motility counts minus baseline, expressed in per cent of the similar result recorded in the parallel PCP control group. The per cent responses are converted to per cent inhibition.

What is claimed:

1. A compound selected from the group consisting of
7-(2-(5,8-dimethyl-[1,2,4]triazolo[1,5-a]pyrazin-2-yl)ethyl)-2,3-dihydro-[1,4]dioxino[2,3-g]quinoline;
6-(2-(5,8-dimethyl-[1,2,4]triazolo[1,5-a]pyrazin-2-yl)ethyl)-[1,3]dioxolo[4,5-g]quinoline;
2-(2-(5,8-dimethyl-[1,2,4]triazolo[1,5-a]pyrazin-2-yl)ethyl)-6-fluoroquinoline; and
2-(2-(5,8-dimethyl-[1,2,4]triazolo[1,5-a]pyrazin-2-yl)ethyl)-7-fluoroquinoline.

2. A compound of claim 1 wherein the compound is 7-(2-(5,8-dimethyl-[1,2,4]triazolo[1,5-a]pyrazin-2-yl)ethyl)-2,3-dihydro-[1,4]dioxino[2,3-g]quinoline.

3. A compound of claim 1 wherein the compound is 6-(2-(5,8-dimethyl-[1,2,4]triazolo[1,5-a]pyrazin-2-yl)ethyl)-[1,3]dioxolo[4,5-g]quinoline.

4. A compound of claim 1 wherein the compound is 2-(2-(5,8-dimethyl-[1,2,4]triazolo[1,5-a]pyrazin-2-yl)ethyl)-6-fluorquinoline.

5. A compound of claim 1 wherein the compound is 2-(2-(5,8-dimethyl-[1,2,4]triazolo[1,5-a]pyrazin-2-yl)ethyl)-7-fluoroquinoline.

6. A pharmaceutical composition comprising a therapeutically effective amount of the compound of claim 1 and a pharmaceutically acceptable carrier, diluent or excipient.

7. A method of treating a neurodegenerative or psychiatric disorder comprising administering a therapeutically effective amount of a compound of claim 1 to a patient in need thereof.

8. The method of claim 7 wherein the psychiatric disorder is schizophrenia, schizophreniform disorder or schizoaffective disorder.

9. The method of claim 8 wherein the schizophrenia is of the paranoid, disorganized, catatonic, undifferentiated or residual type.

10. The method of claim 8, wherein the schizoaffective disorder is of the delusional type or the depressive type.

* * * * *

UNITED STATES PATENT AND TRADEMARK OFFICE
CERTIFICATE OF CORRECTION

Page 1 of 1

PATENT NO. : 9,216,986 B1
APPLICATION NO. : 14/305736
DATED : December 22, 2015
INVENTOR(S) : Jan Kehler et al.

It is certified that error appears in the above-identified patent and that said Letters Patent is hereby corrected as shown below:

In the claims (1)  Column 24, line 3, "fluorquinoline" should read -- fluoroquinoline --.

Signed and Sealed this
Twelfth Day of April, 2016

Michelle K. Lee
*Director of the United States Patent and Trademark Office*